(12) United States Patent
Spratt

(10) Patent No.: US 10,416,474 B2
(45) Date of Patent: Sep. 17, 2019

(54) EYEGLASSES WITH ONE-PIECE SHIELD AND METHOD FOR DESIGNING SAID SHIELD

(71) Applicant: Carl Zeiss Vision International GmbH, Aalen (DE)

(72) Inventor: Ray Steven Spratt, Petaluma, CA (US)

(73) Assignee: Carl Zeiss Vision International GmbH, Aalen (DE)

( * ) Notice: Subject to any disclaimer, the term of this patent is extended or adjusted under 35 U.S.C. 154(b) by 0 days.

(21) Appl. No.: 15/943,588

(22) Filed: Apr. 2, 2018

(65) Prior Publication Data

US 2018/0224668 A1 Aug. 9, 2018

Related U.S. Application Data

(63) Continuation of application No. PCT/EP2015/072713, filed on Oct. 1, 2015.

(51) Int. Cl.
*G02C 7/02* (2006.01)
*A61F 9/02* (2006.01)
*G02C 5/00* (2006.01)

(52) U.S. Cl.
CPC .............. *G02C 7/027* (2013.01); *A61F 9/02* (2013.01); *A61F 9/026* (2013.01); *G02C 5/00* (2013.01)

(58) Field of Classification Search
CPC ........ G02C 7/024; G02C 7/025; G02C 7/027; G02C 7/028
USPC ........................................ 351/159.73–159.77
See application file for complete search history.

(56) References Cited

U.S. PATENT DOCUMENTS

| | | | |
|---|---|---|---|
| 4,859,048 A | 8/1989 | Jannard | |
| 5,652,954 A * | 8/1997 | Paiement | A61F 9/027 2/10 |
| 5,774,201 A | 6/1998 | Tackles | |
| 6,010,217 A | 1/2000 | Houston et al. | |

(Continued)

FOREIGN PATENT DOCUMENTS

| | | |
|---|---|---|
| CN | 1275213 A | 11/2000 |
| CN | 1321906 A | 11/2001 |

(Continued)

OTHER PUBLICATIONS

International search report dated Jun. 30, 2016 of international patent application PCT/EP2015/072713 on which this application is based.

(Continued)

*Primary Examiner* — Robert E. Tallman
(74) *Attorney, Agent, or Firm* — Walter Ottesen, P.A.

(57) ABSTRACT

The invention is directed to non-corrective unitary lens eyeglasses and safety helmets including a one-piece shield and a method for making such a one-piece shield. The method is for designing a one-piece shield for non-corrective unitary lens eyeglasses or a safety helmet, whereby the shield has a front and a back surface, and is computer-implemented with the steps: providing a front surface geometry of the shield; providing a local relationship of the front surface geometry with respect to a center of rotation of a wearer's eye; and, calculating a portion of a back surface geometry attributed to the wearer's eye by establishing non-zero minus power and minimizing prism. The portion of the back surface geometry is a freeform surface geometry.

12 Claims, 5 Drawing Sheets

(56) References Cited

U.S. PATENT DOCUMENTS

| | | | |
|---|---|---|---|
| 6,129,435 | A | 10/2000 | Reichow et al. |
| 6,364,481 | B1 | 4/2002 | O'Connor et al. |
| 6,454,408 | B1 | 9/2002 | Morris et al. |
| 6,709,106 | B2 | 3/2004 | Kelch et al. |
| 7,134,752 | B2 * | 11/2006 | Perrott .................. G02C 7/02 351/159.01 |
| 7,507,358 | B2 | 3/2009 | Morris et al. |
| 8,646,909 | B2 | 2/2014 | Guilloux et al. |
| 8,789,946 | B2 | 7/2014 | Altheimer et al. |
| 8,814,353 | B2 | 8/2014 | Kozu et al. |
| 9,778,486 | B2 | 10/2017 | Kozu et al. |
| 2005/0122470 | A1 | 6/2005 | Perrott et al. |
| 2006/0098161 | A1 | 5/2006 | Dumange et al. |
| 2008/0212019 | A1 | 9/2008 | Reichow et al. |

FOREIGN PATENT DOCUMENTS

| | | |
|---|---|---|
| CN | 102422201 A | 4/2012 |
| CN | 102695979 A | 9/2012 |
| EP | 2407815 A1 | 1/2012 |
| WO | 9952480 A1 | 10/1999 |
| WO | 0004414 A1 | 1/2000 |

OTHER PUBLICATIONS

Written opinion of the international searching authority dated Jun. 30, 2016 of international patent application PCT/EP2015/072713 on which this application is based.

ISO 12311, "Personal protective equipment—Test methods for sunglasses and related eyewear", corrected version Nov. 15, 2013, copyright ISO 2013, published in Switzerland, pp. i to 85.

ISO 12312-1, "Eye and face protection—Sunglasses and related eyewear-", first edition Aug. 1, 2013, copyright ISO 2013, published in Switzerland, pp. i to 23.

Becken, W. et al: Brillenglaeser im Sport—Optimierung der Abbildungseigenschaften unter physiologischen Aspekten, Z.Med. Phys 17 (2007), pp. 56 to 66 (including English translation).

DIN EN 168:2001, Persoenlicher Augenschutz, Personal eye protection-Non-optical test methods, Nichtoptische Pruefvertahren, Deutsche Fassung EN 168:2001, Normenausschuss Feinmechanik und Optik (NA FuO) im DIN Deutsches Institut fuer Normung e.V., Apr. 2002, 36 pages.

Ansi Z80.3-2010, American National Standard for Ophthalmics—Nonprescription Sunglass and Fashion Eyewear Requirements, Nov. 17, 2010, 34 pages.

Standards Australia/Standards New Zealand, Amendment No. 1 to AS/NZS 1067:2003, Sunglasses and fashion spectacles, Jun. 24, 2009, 4 pages.

International Preliminary Report on Patentability of the International Preliminary Examining Authority dated Jan. 17, 2018 of international application PCT/EP2015/072713 on which this application is based.

Written Opinion of the International Preliminary Examining Authority dated Sep. 28, 2017 of international application PCT/EP2015/072713 on which this application is based.

Office Action of the Canadian Intellectual Property Office dated Apr. 30, 2018 in corresponding Canadian patent application 3,000,575.

Office Action of the Australian Intellectual Property Office dated Apr. 20, 2018 in corresponding Australian patent application 2015 410854.

Damon et al: The Human Body in Equipment Design; Harvard University Press, Cambridge, MA, 1966, Revised 1976, ISBN 0674414500, pp. 125 to 130.

First Office action and English translation of the Chinese Office action of the Chinese Patent Office dated Nov. 30, 2018 in corresponding Chinese patent application 201580083601.6.

* cited by examiner

EYEGLASSES WITH ONE-PIECE SHIELD AND METHOD FOR DESIGNING SAID SHIELD

CROSS REFERENCE TO RELATED APPLICATION

This application claims priority of international patent application no. PCT/EP2015/072713 filed Oct. 1, 2015, the entire content of which is incorporated herein by reference.

FIELD OF THE INVENTION

The invention relates to non-corrective unitary lens eyeglasses and safety helmets including a one-piece shield as well as a method for configuring and making such a one-piece shield.

BACKGROUND OF THE INVENTION

A "shield" for unitary-lens eyewear or helmets consists of a single lens. In general, such a "shield" is formed from a transparent material as a single piece, that is a one-piece shield.

Typically, such one-piece shields are configured to curve around the eye to the side of the head ("wrap") and/or tilt inward toward the cheekbone (pantoscopic tilt).

The explanation of this invention will be facilitated by defining some terms used in the following.

A spherical surface is a part of the inside or outside surface of a sphere. A cylindrical surface is a part of the inside or outside surface of a cylinder. A toroidal surface is a surface having mutually perpendicular principal meridians of unequal curvature, of which the cross-section in both principal meridians is nominally circular. An aspherical surface is a part of a surface of revolution having continuously variable curvature from the vertex to the periphery. An atoroidal surface is a surface having mutually perpendicular principal meridians of unequal curvature, of which the cross-section in at least one principal meridian is not circular. Principal meridians of a surface are those meridians of a surface which show the maximum and minimum curvatures on measurement. A progressive surface is a surface, which is non-rotationally symmetrical, with a continuous change of curvature over part or all of the surface, generally intended to provide increasing addition or degression power.

A freeform surface distinguishes from the above spherical, cylindrical, toroidal, aspherical and atoroidal surfaces. A freeform surface is a surface without symmetry over an area. Progressive surfaces as defined above having in addition in particular no mirror symmetry may be freeform surfaces. Most computerized modelling systems today use non-uniform rational B-spline (NURBS) mathematics to describe the surface forms; however, there are other methods such as bicubic splines or Gorden surfaces or Coons surfaces.

A plano lens is a lens with nominally zero dioptric power. A spherical lens is a lens with two spherical surfaces. A cylindrical lens is a lens with at least one cylindrical surface. A toric lens is a lens with at least one toroidal surface. An aspheric lens is a lens with at least one aspherical surface. An atoric lens is a lens with at least one atoroidal surface.

An ophthalmic lens is a lens intended to be used for purposes of measurement, correction and/or protection of the eye, or for changing its appearance. A spectacle lens is an ophthalmic lens worn in front of, but not in contact with, the eyeball. A corrective lens is a spectacle lens with dioptric power. A non-corrective lens is a spectacle lens with no dioptric power or such low dioptric power that it is nominally not used for corrective purposes.

The front surface of a spectacle lens is that surface of the spectacle lens intended to be fitted away from the eye. Accordingly, the back surface of a spectacle lens is that surface of the spectacle lens intended to be fitted nearer to the eye.

Focal power is a general term comprising the spherical and astigmatic vertex powers of a spectacle lens. Back vertex power is the reciprocal of the paraxial back vertex focal length measured in meters. Spherical power is a value of the back vertex power of a spherical-power lens or the vertex power in one of the two principal meridians of an astigmatic-power lens, depending on the principal meridian chosen for reference.

Prismatic deviation is the change in direction imposed on a ray of light as a result of refraction. Prismatic effect is the collective name for the prismatic deviation and base setting (that is the setting position for the prism base). Prismatic power is the prism value of the prismatic effect at the design reference point.

Dioptric power is a general term comprising the focal power and the prismatic power of a spectacle lens.

Optical axis is a straight line, perpendicular to both optical surfaces of a spectacle lens, along which light can pass undeviated. Vertex is the point of intersection of the optical axis with a surface of a lens. Therefore, back vertex is the point of intersection of the optical axis with the back surface of a lens.

The line of sight is the line joining the center of the fovea to the center of the exit pupil of the eye, and its continuation from the center of the entrance pupil forward into object space.

The normal line of sight is a fixed line that projects forward from the eye along the line extending straight ahead of the eye in the primary position with the head looking straight ahead. The line of sight is not normally understood to vary in a given individual. However the normal line of sight may vary (both horizontally and vertically) between individuals, because of variations of head and face morphologies (such as the distance between the eyes, and the location of the nasion and ears) which determine an as worn orientation of eyewear. Moreover, the normal line of sight may vary vertically between the right and left eye of a given individual, because of facial asymmetry. The "normal" line of sight is therefore often determined on a standardized head form, such as the Alderson head form, or the more current and accurate Canadian head form, in which a statistically average position of a line of sight has been determined.

A visual point is a point of intersection of the line of sight with the back surface of a lens. The distance visual point is the assumed position of the visual point on a lens, which is used for distance vision under given conditions. This is usually assumed to be the intersection of the line of sight with the lens, the eyes being in the primary position with the head erect.

The back vertex distance is the distance between the back surface of the lens and the apex of the cornea, measured with the line of sight perpendicular to the plane of the spectacle front.

The main fixation direction is the most common direction of the line of sight relative to the primary position.

Primary position is the position of the eye of a human relative to the head, looking straight ahead at an object at eye level. Monocular pupillary distance is the distance between the center of the pupil and the mid-line of the bridge of the nose or the spectacle frame when the eye is in the primary position.

The "as-worn" pantoscopic angle is the angle in the vertical plane between the normal to the front surface of the spectacle lens at its boxed center and the line of sight of the eye in the primary position.

Lateral wrap is the curvature or twist of a spectacle lens around the eye to the side of the head. The wrap angle, also known as face form angle or panoramic angle is the angle between the plane of the spectacle front and the plane of the right lens shape, or of the left lens shape. The right or left face form angle is regarded as positive if the temporal side of the right or left lens plane is closer to the head than the plane of the spectacle front.

A "nasal" direction is generally toward the nose, and a "temporal" direction is generally toward the temple. A "superior" direction is generally upward and an "inferior" direction is generally downward.

A lens produces a linear displacement, or foreshortening, of an image if the image is viewed along a direction of gaze that is not along the optical axis of the lens nor along the normal to the surface of the lens.

Prismatic deviation likewise may be induced if the direction of gaze is not parallel to the optical axis, regardless of where on the lens the direction of gaze intersects the surface. When the direction of gaze is not coincident with the optical axis of a lens, the lens will typically produce a total deviation, which is a combination of foreshortening and prismatic deviation.

Conventionally, the amount of the prismatic deviation is measured in prism diopters (PD or D).

One prism diopter is the unit of prismatic deviation, equal to $100 \tan \delta$, where $\delta$ is the angle of deviation, in degrees (°). The prism diopter is a deviation measured in centimeters at a distance measured in meters. Prism diopters can therefore also be expressed in centimeters per meter (cm/m). The decentration can be horizontal, vertical, or oblique, but is generally evaluated in terms of horizontal and vertical deviations. A horizontal decentration of a non-plano lens with respect to an eye generally produces a horizontal prismatic deviation. A nasal decentration of a positive power lens produces a prismatic deviation that is referred to as "base-in" prism. Similarly, a temporal decentration of a positive power lens produces a prismatic deviation referred to as "base-out" prism. Nasal and temporal decentrations of minus power lenses produce base-out and base-in prism, respectively.

To compensate for horizontal prism in eyewear, the eyes must rotate horizontally by angles approximately equal to the prismatic deviations. If the prismatic deviations for both eyes have the same magnitude and direction, the normal line of sight is deviated, but the eyes move in a so called "yoked" alignment. If the prismatic deviations differ in magnitude or direction, a relative motion of an eye or eyes toward (convergence) or away from each other (divergence) is required to avoid diplopia (double vision). The differences in prismatic deviation thus give rise to a disjunctive or vergence demand that is quantified as the net prismatic deviation obtained by combining the individual prismatic deviations. The vergence demand can require either a convergence or a divergence of the eyes, but is referred to as a vergence demand in either case. Wearers are more comfortable if the yoked and vergence demands are kept small in order to permit accurate spatial perception and anticipation timing, and to avoid eye fatigue.

The vergence resulting from prismatic deviations for both eyes depends on both the magnitude and direction of the prismatic deviations.

If the amount of prism induced for each eye is the same, the eyes will move together in a "yoked" rotation. If the amount of prism for each eye is not equal, then an additional vergence demand is imposed on the eyes, in which there must be relative movement of one or both of the eyes toward (convergence) or away (divergence) from each other. Such vergence is often incomplete, which can result in diplopia or poor perception. Even if the vergence is complete, it induces oculomotor strain that is uncomfortable for the wearer.

Vertical prism effects are generally divided into base-up and base-down prism. The same problems discussed with respect to base-out and base-in prism apply to vertical prism. Differences in vertical prism are not well tolerated, but "yoking" type prism, the same for both eyes, are well tolerated.

The amount of horizontal prism can vary across the lens, and imbalance can become more of a problem peripherally, where one eye is looking through a nasal portion of a lens while the other eye is looking through a temporal portion of the lens. The amount of vertical prism can also vary across the lens in a similar fashion when the eye is looking through a superior or inferior portion of the lens. This variation can create inaccuracies in visual perception across the field of view that are difficult to compensate, and are troublesome in recreational or sporting activities that demand accurate visual input.

There are a plurality of patents, patent applications and other documents dealing with shape and arrangement of one-piece shields in front of wearer's eyes, the respective influence on aesthetic aspects as well as the respective resulting optical properties and impact on wearer's visual impression. Some of these documents are herewith presented in the following.

U.S. Pat. No. 4,859,048 discloses a cylindrical lens for use in a pair of sunglasses, comprising a unitary pane of transparent material curved about an axis and having a substantially constant radius such that the lens defines a portion of the wall of a cylinder. The lens covers both eyes of the wearer and effectively shields the eyes from peripheral as well as direct bright light. The lens may have either a uniform thickness throughout, or may taper from a greater thickness in a region centered about the midpoint, generally above the nose of a wearer, to a lesser thickness near the peripheral ends of the lens. The unitary lens has an upper edge and a lower edge, whereby the lower edge has a nosepiece opening formed therein for mounting the lens on the nose of a wearer.

U.S. Pat. No. 5,774,201 discloses a lens for unitary-lens eyewear. The lens has an outer, convex surface, and an inner, concave surface, and a thickness therebetween. At least one of the outer, convex surface and the inner, concave surface has an arcuate cross-sectional configuration conforming substantially to an ellipse having an eccentricity. The lens may have any of a variety of configurations in the vertical planes, independent of the horizontal elliptical shape. Additionally, the lens may be of uniform thickness or of tapering thickness from a relatively thicker medial portion to thinner lateral portions. The lens has an upper edge and a lower edge, and the lower edge has a nosepiece opening formed therein for mounting the lens on the nose of a wearer. Such lenses do not comply with contemporary aesthetic requirements.

Therefore, nowadays, the surfaces of conventional shields are typically spherical or toroidal, that is, they have circular horizontal and vertical cross-sections at the center. Such a shield must be "tapered" if it is to have zero optical power. A one-piece shield like this with zero optical power, that is a toroidal plano lens, automatically has zero prism imbalance between the two eyes. The optical properties of such shields do only comply with present requirements in a specific arrangement in front of a wearer's eyes. In particular, if such lenses are wrapped and oriented with tilt, a wearer's perception is distorted.

U.S. Pat. No. 6,010,217 discloses an optically corrected shield for unitary lens eyeglasses or safety helmets. The preferred lens (shield) geometry may be either spherical or toroidal. In particular, at least the front surface of the shield conforms either to a portion of the surface of a sphere or a portion of the surface of a toroid. The shield has a front surface which conforms in a vertical plane to a portion of a first circle having a first center and the shield has a rear surface which conforms in the vertical plane to a portion of a second circle having a second center. The first and second centers are non-coincident, and lie on an optical axis which extends through the shield. The lens is oriented on the head of the wearer by a frame or helmet that provides both wrap and pantoscopic tilt but maintains the lens in a position such that the optical axis is maintained substantially in parallel to the normal sight line of the wearer. The parallel relationship between the optical centerline and normal line of sight was found to be partially successful in minimizing optical distortion caused by wrap and pantoscopic tilt, but these lenses still had undesired peripheral performance, with prismatic effects that produced yoked and vergence demands.

The document outlines that instead of spherical or toroidal front and back surfaces other lens geometries such as elliptical or aspheric may also be utilized. However, a detailed description of such lens geometries is missing in this document.

U.S. Pat. No. 6,129,435 disclose non-corrective protective eyewear with lateral wrap and pantoscopic tilt comprising lenses having an optical axis that is deviated away from the line of sight, in a direction generally opposite the inward tilt of the lateral wrap (horizontal tilt) and/or the incline of pantoscopic tilt (vertical tilt), to offset the tilt induced (horizontal and vertical) prism (see in particular FIGS. 11 and 12 and the explanation given therein). In particular the optical axis is angularly deviated at a sufficient angle away from parallel with the line of sight to minimize prismatic distortion, both along a line of sight and peripherally in the field of view.

According to the teaching of the above publications, low power may be introduced into the lenses to decrease their taper, further offset the tilt induced prism and astigmatism (particularly in peripheral fields of view), lessen weight, provide better physical stability, and allow more uniform light transmission than plano lenses. The document outlines that prism by tilt can be reduced by one or more of a combination of parameters, such as increasing the angle of deviation between the line of sight and optical axis, increasing the minus power of the lens, or reducing the base curvature of the lens. According to U.S. Pat. No. 6,129,435 the lenses having such parameters may be spherical, cylindrical, toroidal, elliptical, or of other not further specified configurations.

U.S. Pat. No. 6,454,408 B1 discloses an optical lens element being, for example, adapted for mounting in a frame of the shield type including first and second surfaces of complementary curvature. At least one surface exhibits a deviation in curvature from a standard optical surface of spherical or toric shape along the horizontal meridian inducing optical distortions such as astigmatism of more than 1.0 D. The first and second surfaces in combination define an optical zone exhibiting mean through power along at least one meridian being constant within ±0.25 D. This document discloses that the curvatures of the first and second surfaces may be smoothly varying functions that allow the surfaces of the optical lens element to deviate substantially from, for example, a conventional conic section whilst providing between them constant mean through power within ±0.25 D through the lens. That is, the surfaces of the optical lens element are disclosed as being asymmetric.

U.S. Pat. No. 6,364,481 B1 discloses in particular plano lenses for use in glasses of the wrap-around or shield type. The lenses may include a spherical, an aspheric, a toric, an atoric surface or any combination thereof or any other complex form and may exhibit an astigmatic correction. The lenses comprise a peripheral temporal zone which includes a prismatic correction to improve the overall field of vision of the wearer. The front and/or back surface of the optical lenses may further include a surface correction to at least partially compensate for prismatic errors in the primary line of sight (the zone of 'straight-ahead' vision). The surface correction may be a prismatic correction, in particular a base-in or base-nasal correction applied to the front and/or back surface.

Two further approaches of unitary eyewear to improve visual performance for the wearer known from prior art are described in the following with reference to FIGS. 1A, 1B, 2A and 2B. FIG. 1A shows a perspective view of a first example of non-corrective unitary lens eyeglasses 100 with a one-piece shield 102 and a frame 104 supporting the shield 102. FIG. 1B shows a horizontal cross-section of the shield 102 in a plane above the nosepiece opening 106. FIG. 2A shows a perspective view of a second example of non-corrective unitary lens eyeglasses 200 with a one-piece shield 202 and a frame 204 supporting the shield 202. FIG. 2B shows a horizontal cross-section of the shield 202 in a plane above the nosepiece opening 206.

If a spherical or toroidal shield has a single optical axis, and zero back vertex power, it will also have zero prism as worn when looking parallel to the optical axis. However, this zero prism criterion is not fulfilled everywhere for the rotating eye at any specific pupil distance. If the shield has two separate optical axes, one for each eye, then wrap and curvature can be decoupled. However, in the case the two halves of the shield would not meet smoothly in the center. FIGS. 1A, 1B, 2A and 2B show lens eyeglasses 100, 200 having such shields 102, 202 consisting of two halves each having its own optical axis. The shield-halves 102a, 102b and 202a, 202b, respectively, the shields 102 and 202 are composed of, each are spherical or toroidal, and each have a separate optical axis which is parallel to the line of sight. Each of these shield-halves 102a, 102b and 202a, 202b are tapered toward the temples. The shield 202 according to the second example comprises a broad not-optically-corrected feature 208 above the nose piece 206 instead of purely "butting" the two shield-halves 102a, 102b up against each other. The individual shield-halves 202a, 202b in these safety goggles 200 are also spherical or toroidal.

Due to cosmetic reasons the non-corrective unitary lens eyeglasses 100, 200 shown in FIGS. 1A, 1B, 2A and 2B may not be used for all purposes. Therefore, alternative solutions are required in order to fulfill both aesthetic and optical needs.

Becken et al: "Brillenglaser im Sport: Optimierung der Abbildungseigenschaften unter physiologischen Aspekten", Zeitschrift für medizinische Physik, Urban and Fischer, Jena, Deutschland, vol. 17, no. 1, of May 3, 2007, pages 56-66 discloses individualized mathematical optimization procedures for corrective sports spectacle lenses.

US 2006/0098161 A1 discloses a unitary single lens or shield. The shield has left and right lens portions, respectively, each having a visual center positioned in the line of sight of the left and right eyes of the wearer in the as worn condition. In this regard, each of the lens portions is individually constructed. Each lens portion has a visual center, a central area, and a peripheral area, and both the convex and concave sides of the lens are configured accordingly. The inner concave surface of each portion may be defined as an aspheric NURBS surface. The document discloses to improve peripheral vision in the case of spherical lenses, cylindrical and toric lenses, and as an extension of the invention may be applied to any shape (free form).

This document also discloses a method of manufacturing a non-corrective optical lens blank adapted for mounting in eyewear after appropriate glazing, the method comprising the steps of: configuring an outer convex surface of the lens blank; configuring an inner concave surface of the lens blank; defining a reference axis relative to the outer convex surface; defining a visual axis relative to the reference axis; defining a visual area surrounding the visual axis, the visual axis showing the location where the visual area is intended in the as worn position; and modifying the inner concave surface such so as to improve optical quality of the lens such whereby the modified inner concave surface has continuous horizontal and vertical curvatures in both horizontal and vertical meridians, but of varying dimension. The method will not modify the general torical shape of the lens, but rather only one or both of the surfaces in such a way that the general Gullstrand shape is not changed.

Despite the unitary single lens or shield disclosed in this document having proven its worth, there is a need of further improvement.

SUMMARY OF THE INVENTION

In view of the foregoing, it is an object of the invention to provide non-corrective unitary lens eyeglasses and a safety helmet including a one-piece shield and a frame (for example, with temple arms) in which the one-piece shield is mounted or a one-piece "framed" shield with temple arms, the one-piece shield or the one-piece "framed" shield fulfills both aesthetic and optical needs of the wearer. Related to the above, it is a further object of the invention to provide a method for designing and a method for making such a one-piece shield or such a one-piece "framed" shield.

The non-corrective unitary lens eyeglasses or safety helmet for a wearer includes: a one-piece shield; the one-piece shield defining a front surface having a front surface geometry and defining a back surface having a back surface geometry; a frame wherein the one-piece shield is mounted or which forms an integral part of the one-piece shield; the frame being configured to dispose the one-piece shield in a predetermined local relationship with respect to the wearer's head and eyes; the wearer's head being one of a plurality of standardized head models of the group including: a head model having the Alderson headform, a head model having the headform according to EN 168, a head model having the headform according to ISO 12311:2013, a head model having the headform according to ISO 12312-1 and a head model having the Canadian headform; the standardized head models each having left and right eyes being located at standardized positions thereby providing respective standardized theoretical centers of rotation of the left and right eyes; respective standardized theoretical monocular pupil distances; and, respective standardized normal lines of sight; and, the one-piece shield being disposed in the predetermined local relationship with respect to the wearer's head and eyes establishing non-zero minus power and prism as worn of less than 0.15 prism diopter within a portion of the back surface surrounding an intersection of wearer's standardized normal line of sight of one of the wearer's eyes with the back surface for all of wearer's lines of sight intersecting the back surface within the portion due to eye rotations of the one of the wearer's eyes around the respective standardized theoretical center of rotation of the one of the wearer's eyes, wherein the non-zero minus power within the portion is less than 0.12 D, wherein the portion is larger than 0.1 cm$^2$, wherein the portion of the back surface has a freeform surface geometry.

According to the invention, the non-corrective unitary lens eyeglasses or the safety helmet includes a one-piece shield as defined above and a frame in which the one-piece shield is mounted. Alternatively, the non-corrective unitary lens eyeglasses or the safety helmet includes a one-piece "framed" shield. The difference between a one-piece shield and a one-piece "framed" shield is that the one-piece shield is mounted in a frame which carries the temple arms while the one-piece "framed" shield is a frame and a shield in a single piece.

The one-piece shield or the one-piece "framed" shield has a front surface and a back surface. The front surface has a front surface geometry and the back surface has a back surface geometry.

The one-piece shield has a front surface which is curved in horizontal direction between the point where the "normal" straight ahead line of sight of the left eye intersects the front surface and the point where the "normal" straight ahead line of sight of the right eye intersects the front surface without having any kink or change of direction of curvature. Preferably, between these two points of intersection of the front surface at least the front surface is of unitary toroidal, ellipsoidal, or conicoid (ellipse, hyperbola, parabola et cetera) shape.

Irrespective of whether the preferred features outlined in the preceding paragraph are fulfilled, the one-piece shield may have a mean curvature of the front surface to be 6.5 D or greater at the point where the "normal" straight ahead line of sight intersects that front surface. It may further have a thickness of at least 1.95 mm, preferably more than 2.05 mm, more preferably more than 2.15 mm, most preferably more than 2.25 mm measured normal to the front surface at that point.

The frame (on which the one-piece shield is mounted or which forms an integral part of the one-piece "framed" shield) is constructed to dispose the one-piece shield in a predetermined local relationship with respect to a wearer's head and eyes. It is assumed that the wearer's head is one of a plurality of standardized head models of the group consisting of a head model having the Alderson headform, a head model having the headform according to EN 168, a head model having the headform according to ISO 12311: 2013, which is incorporated herein by reference, a head model having the headform according to ISO 12312-1, which too is incorporated by reference, and a head model having the Canadian headform. Such standardized head models are generally used to define optical properties of average consumers. It may be compared with standardized sizes of garments which are more or less suitable for different groups of the human population.

In particular the Alderson eyeglass dummy headforms were developed from Alderson Research Laboratories' VIP dummy heads. The VIP dummies were developed for automotive crash testing to comply with NHTSA requirements from 1966 through 1972. Modifications to the head and ears were made to enhance the headforms' ability to hold eyeglasses in place. The headforms were modeled from human subjects whose height and weight put them in certain percentile groups. These percentiles were developed from anthropometric surveys during and after World War II. Data supporting these percentile groups appears in: The Human Body In Equipment Design, by Damon, Albert; Stoudt, Howard W.; McFarland, Ross Armstrong. Harvard University Press, Cambridge Mass. 1971. Revised 1976 ISBN 0674414500.

Each standardized head model and therefore also the concrete headform having been selected for configuring and fabricating the respective eyeglasses or helmet claimed and described above has left and right eyes being located at standardized positions thereby providing respective standardized theoretical centers of rotation of the left and right eyes, respective standardized theoretical monocular pupil distances and respective standardized "normal" lines of sight for each eye. Assuming in the following that the respective eyeglasses or helmet is held in place by the frame on the concrete standardized headform there is one single predetermined relationship between the one-piece shield and the eyes of the headform. This means the one-piece shield is oriented and distanced from the left and right eyes of the headform in a predetermined manner, that is, in the predetermined local relationship for which it was configurated and fabricated before.

In case the one-piece shield is disposed in the predetermined local relationship with respect to the wearer's head and eyes the one-piece shield establishes non-zero minus power and prism as worn of less than 0.15 prism diopter within one or two specific portions of the one-piece shield for the wearer when rotating his eyes. This portion (attributed to one eye) is or these two portions (each being attributed to another eye of the wearer) are located at the back surface of the shield and each portion is defined by a certain area surrounding an intersection of wearer's standardized "normal" line of sight of one of the wearer's eyes with the back surface, namely the respective distance visual point as defined in the introductory part of the specification. The non-zero minus power criterion is a power of less than 0.12 D. According to the present invention the portion or the portions described above is/are larger than 0.1 cm² in size.

Therefore, the non-zero minus power and less than 0.15 prism diopter criterion applies for all of wearer's lines of sight intersecting the back surface within the portion due to eye rotations of the one of the wearer's eyes around the respective standardized theoretical center of rotation of the one of the wearer's eyes.

The portion or, as the case may be, the two locally separated and not intersecting portions of the back surface in addition are defined by a respective surface geometry, which according to the invention is a freeform surface geometry.

The front surface of the (as the case may be "framed") shield may be of any shape and geometry. In particular, preferably the front surface has a (unitary) toroidal surface geometry, an atoroidal surface geometry, an aspheric surface geometry or an ellipsoidal surface geometry as defined above. In a preferred embodiment the front surface has a "freeform" geometry. If the front surface has a "freeform" geometry both adjustment according to aesthetic requirements as well as optical requirements is possible.

The shield may comprise a nose opening similar to the nose openings 106, 206 shown in FIGS. 1A and 2A. It may also comprise nose pads attached thereon.

The shield may be made of any kind of transparent material. It may be made of organic compounds such as polycarbonate or polyallyldiglycolcarbonate. The materials may comprise dyes or functional layers such as polarizing sheets et cetera.

The shield may be covered by one or a plurality of functional layers such as scratch resistant layers, antireflective coatings, coloring coatings, polarizing coatings, phototropic coatings et cetera.

In a preferred embodiment of the present invention the portion or the portions described above is/are larger than 0.25 cm², preferably larger than 0.5 cm², more preferably larger than 0.75 cm². The larger the size the less the respective wearer of such non-corrective unitary lens eyeglasses or safety helmet will feel discomfort.

Each predetermined portion may be surrounded by another predetermined portion in which the less than 0.15 prism diopter criterion is no more fulfilled. Nevertheless, in another predetermined portion the non-zero minus power criterion with a power of less than 0.12 D, preferably less than 0.09 D and more preferably less than 0.05 D may still be fulfilled. It is preferred that another predetermined portion is more than 3 cm² in size. More preferably another predetermined portion is more than 4 cm² in size. Most preferably another predetermined portion is more than 5 cm² in size.

The non-corrective unitary lens eyeglasses or safety helmet according to the invention may be equipped with a shield. The portion/portions thereof as defined above establish non-zero minus power of less than 0.25 D, preferably less than 0.12 D, more preferably less than 0.09 D and most preferably less than 0.05 D.

The non-zero minus power (that is, non-zero mean power (with zero astigmatism)) being established in the portion/portions as defined above may exceed a value of 0.01 D, preferably of 0.03 D and more preferably of 0.04 D. The inventor found out that a non-zero minus power value in the range between 0.02 D and 0.09 D is most comfortable for most of the wearers.

As already explained in the introductory part of the specification prism as worn should be minimized in order to minimize distortion and avoid discomfort for the wearer. Nevertheless, compliance with aesthetical needs is in contradiction within a certain degree to this requirement. Therefore, it may be acceptable if prism as worn is less than 0.10 prism diopter, preferably less than 0.08 prism diopter, more preferably less than 0.06 prism diopter and most preferably less than 0.05 prism diopter.

Each non-corrective unitary lens eyeglasses or safety helmet, and in particular the shield thereof, according to the invention is configurated and fabricated that the non-zero minus power and less than 0.15 prism diopter criterion within the portion(s) applies for one single back vertex to center of rotation distance, that is, one single distance between the back vertex to the standardized theoretical center of rotation of one of the wearer's eyes, within the range between 22 mm and 32 mm, preferably between 24 mm and 30 mm, more preferably between 26 mm and 28 mm and most preferably 27 mm. In particular, preferably there may be three different kinds of shields which are optimized (that is, fulfill above criterion) for back vertex to center of rotation distance values of either 24 mm, 27 mm or 30 mm, respectively.

Each non-corrective unitary lens eyeglasses or safety helmet, and in particular the shield thereof, according to the invention is configured and fabricated that the non-zero minus power and less than 0.15 prism diopter criterion within the portion(s) applies for one single monocular pupil distance in the range between 28 mm and 36 mm, preferably between 30 mm and 34 mm, more preferably between 31 mm and 33 mm and most preferably 32 mm. In particular, preferably there may be three different kinds of shields which are optimized (that is, fulfill above criterion) for monocular pupil distance values of either 28 mm, 32 mm or 36 mm, respectively.

A computer-implemented method for configuring a one-piece shield for non-corrective unitary lens eyeglasses or safety helmets, wherein the shield has a front surface and a back surface, includes the following steps:

providing a front surface geometry of the shield;
providing a predetermined local relationship of the front surface geometry with respect to a predetermined center of rotation of at least one of a wearer's eyes; and,
calculating a predetermined portion of a back surface geometry of the shield attributed to the at least one of the wearer's eyes by establishing non-zero minus power and minimizing prism as worn for a plurality of wearer's lines of sight intersecting the back surface within the predetermined portion and the front surface due to eye rotations of the at least one of the wearer's eyes around the predetermined center of rotation of the at least one of the wearer's eyes, whereby the predetermined portion of the back surface geometry is a freeform surface geometry.

The complete method may be installed as a computer-simulation based on front surface geometry data and position data of a predetermined center of rotation of at least one of a wearer's eyes relative to the position and orientation of the front surface represented by the surface geometry data.

It is assumed or given to the computer conducting the simulation that the non-zero minus power (that is, mean power with zero astigmatism) is smaller than 0.12 D. Preferably the non-zero minus power is assumed or given to be smaller than 0.09 D and more preferably smaller than 0.05 D. The expected discomfort for the wearer wearing a so configurated shield in the predetermined manner is reduced with the smaller value for the non-zero minus power.

It may be assumed or given to the computer conducting the simulation that the non-zero minus power exceeds a value of 0.01 D, preferably of 0.02 D and more preferably of 0.03 D. The expected discomfort for the wearer wearing a so configurated shield in the predetermined manner is reduced with the increased value for the non-zero minus power.

The method may in addition be characterized in that the minimizing prism includes minimizing vertical prism as worn and/or minimizing horizontal prism as worn. Preferably, both vertical prism as worn and horizontal prism as worn should be minimized.

The method according to the invention may in particular be characterized in that the plurality of wearer's lines of sight intersecting the back surface within the predetermined portion and the front surface due to eye rotations of the at least one of the wearer's eyes around the predetermined center of rotation of the at least one of the wearer's eyes for which non-zero minus power is established and prism is minimized comprise more than 10 different wearer's lines of sight, preferably more than 20 different wearer's lines of sight and most preferably more than 30 different wearer's lines of sight. The different wearer's lines of sight for calculation may be arranged in a regular equidistant angular "grid" centered in the center of rotation of the respective eye. The calculation engine may use a ray tracing method.

The predetermined portion, in which the optical properties are to be achieved, may be more than $0.10\ cm^2$ in size. Preferably more than $0.25\ cm^2$ in size, and most preferably more than $0.50\ cm^2$ in size may be used for calculation.

The predetermined portion may be less than $2.5\ cm^2$ in size, preferably less than $2.0\ cm^2$ in size, more preferably less than $1.5\ cm^2$ and most preferably less than $1.0\ cm^2$ in size.

The predetermined portion may be surrounded by another predetermined portion in which the less than 0.15 prism diopter criterion is no more fulfilled. Nevertheless, in another predetermined portion the non-zero minus power criterion with a power of less than 0.25 D, preferably less than 0.12 D, more preferably less than 0.09 D and most preferably less than 0.05 D may still be fulfilled. It is preferred that another predetermined portion is more than $3\ cm^2$ in size. More preferably another predetermined portion is more than $4\ cm^2$ in size. Most preferably another predetermined portion is more than $5\ cm^2$ in size.

As already mentioned above, the predetermined portion attributed to the at least one of the wearer's eyes and the predetermined portion attributed to the other of the wearer's eyes preferably do not intersect each other.

The method according to the invention may be characterized in that the calculating step comprises that zero vertical prism as worn and zero horizontal prism as worn is established for at least one predetermined wearer's line of sight. Preferably the at least one predetermined line of sight is at least one of the theoretical straight ahead line of sight, a measured straight ahead line of sight of an individual, a theoretical functional line of sight and a measured functional line of sight of an individual. That is, both theoretical lines of sight which may correspond to an average wearer (that is, being, for example, related to a standardized head model) or individual lines of sight which are determined for a specific individual may be used providing zero vertical prism as worn and zero horizontal prism as worn to a wearer.

The invention is also directed to a method for making a one-piece shield for non-corrective unitary lens eyeglasses or safety helmets, whereby the shield has a front surface and a back surface which includes the steps: designing the shield using a method according to one of the embodiments described above; and, molding the shield as a single molded piece.

In particular, the shield may be a "framed" shield as described and defined above.

According to the invention, the method may be stored as a computer program. Therefore, the invention also covers a computer program comprising a program code for execution of all method steps according to one of the embodiments described above in detail, if the computer program is loaded in a computer and/or executed in a computer.

In particular, a computer readable storage medium may have a computer program stored thereon, wherein the computer program includes a program code for execution of all method steps according to one of the embodiments described above, if the computer program is loaded in a computer and/or executed in a computer.

BRIEF DESCRIPTION OF THE DRAWINGS

The invention will now be described with reference to the drawings wherein.

DESCRIPTION OF THE PREFERRED EMBODIMENTS OF THE INVENTION

Figure 1A:
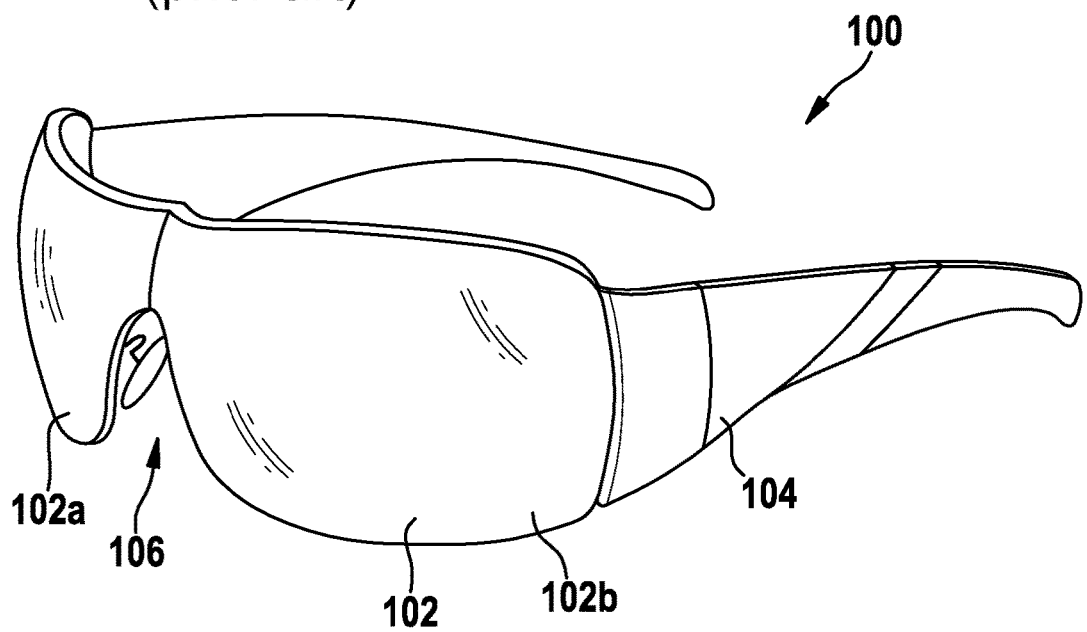
FIG. 1A is a perspective view of a first example of non-corrective unitary lens eyeglasses with a one-piece shield and a frame supporting the shield according to the prior art.
Figure 1B:
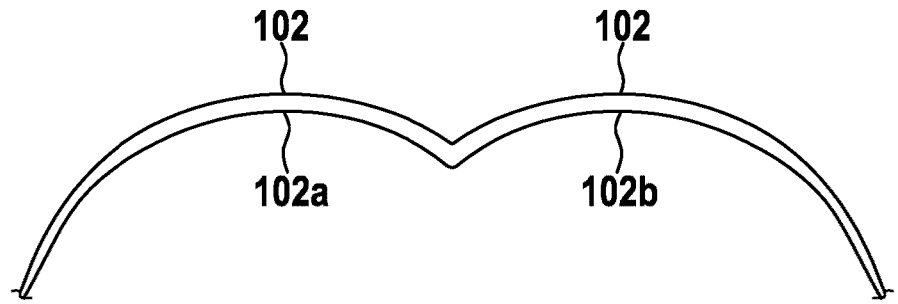
FIG. 1B is a horizontal cross-section of the shield of the non-corrective unitary lens eyeglasses shown in FIG. 1A in a plane above the nosepiece opening.
Figure 2A:
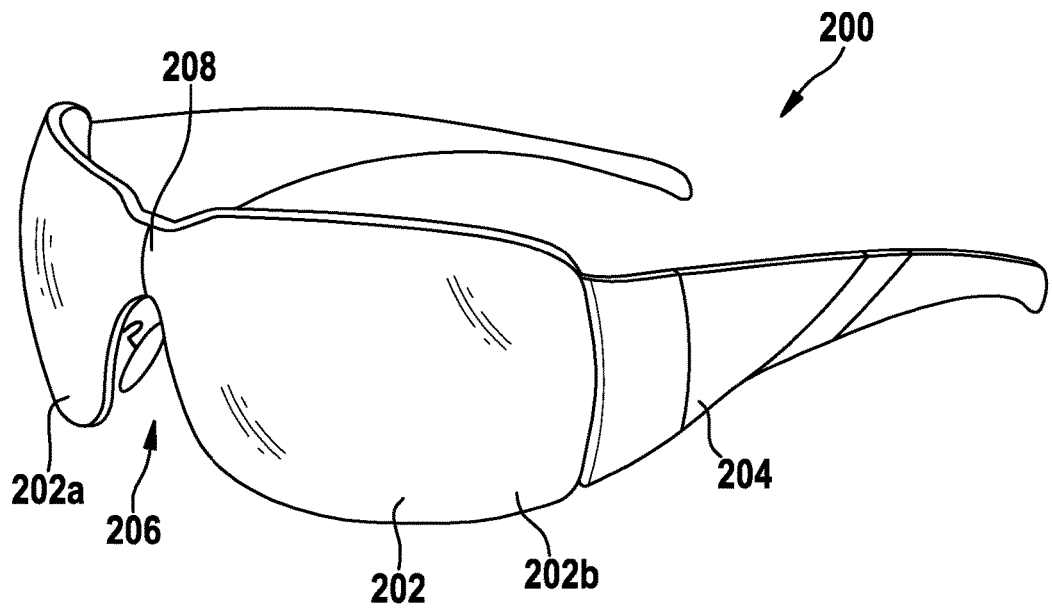
FIG. 2A is a perspective view of a second example of non-corrective unitary lens eyeglasses with a one-piece shield and a frame supporting the shield according to the prior art.
Figure 2B:
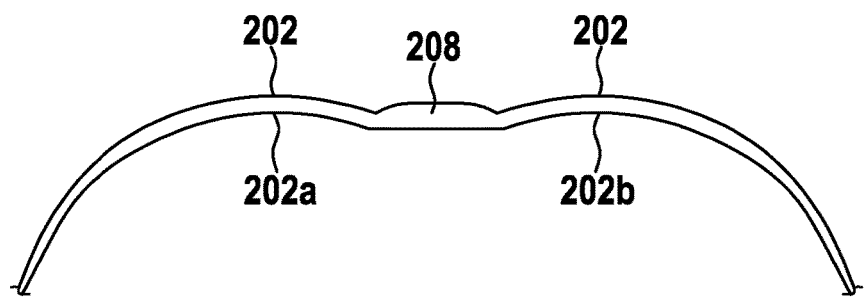
FIG. 2B is a horizontal cross-section of the shield of the non-corrective unitary lens eyeglasses shown in FIG. 2A in a plane above the nosepiece opening.
Figure 3:
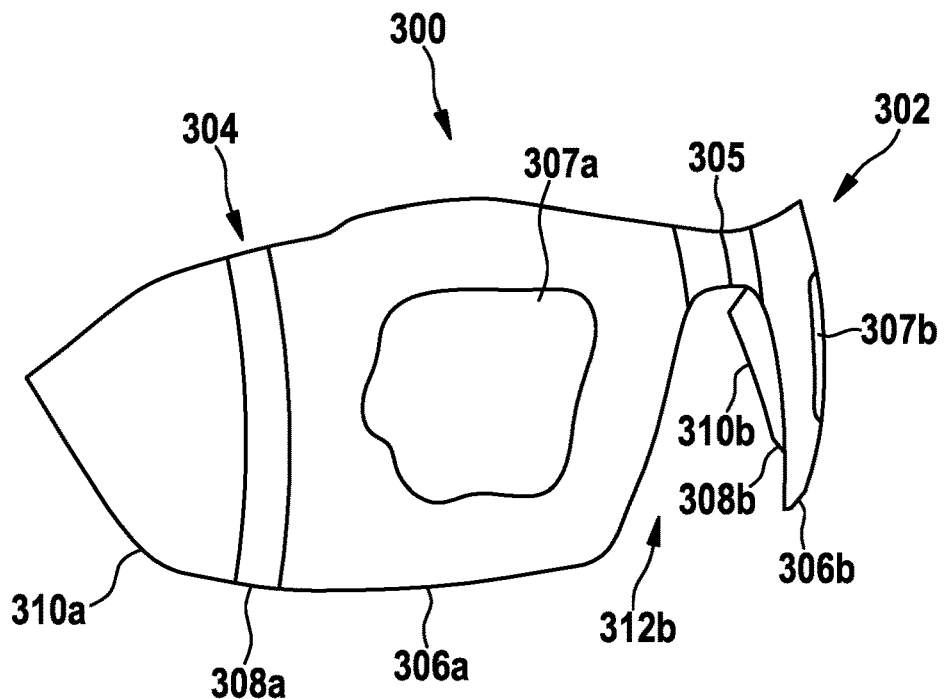
FIG. 3 is a perspective view of a first embodiment of a one-piece "framed" shield according to the invention for non-corrective unitary lens eyeglasses.

FIG. 3 shows a perspective view of a first embodiment of a one-piece "framed" shield 300 according to the invention for applying temple arms thereon (not shown) of non-corrective unitary lens eyeglasses (not shown). The shield being molded together with a frame as a single piece has a front surface 302 and a back surface 304. The front surface 302 has a predefined front surface geometry. In the present embodiment, the front surface has a free-formed shape.

The back surface geometry of the back surface 304 has different zones or portions 305, 306a, 306b, 307a, 307b, 308a, 310a, 310b which may be distinguished by its respective local/areal geometries.

The frame together with the temple arms, which are not shown, is constructed to dispose the one-piece shield 300 in a predetermined local relationship with respect to a wearer's head and eyes. In the present embodiment the frame and temple arms are shaped to comply to an Alderson head form. This means that the shape of the frame and temple arms have a geometry such that the non-corrective unitary lens eyeglasses are held in a predetermined position on a wearer's head having the shape of an Alderson head form.

The eyes of the Alderson head form are located at standardized positions thereby providing respective standardized theoretical centers of rotation of the left and right eyes (the standardized theoretical value for the location of the center of rotation is 15 mm behind the respective cornea; with respect to the present invention a variance of ±2 mm may be possible), respective standardized theoretical monocular pupil distances and respective standardized "normal" lines of sight. As a consequence, the pre-defined front surface of the shield 300 may be positioned with respect to the eyes of the Alderson head form or the eyes of the "average wearer" in a predetermined manner. Therefore, the back surface geometry may be adjusted to the requirements of a wearer having a head corresponding to the Alderson head form.

The shield 300 according to the invention is configured and fabricated for an "average wearer" having a head being shaped according to the Alderson head form and having his eyes positioned in the same manner as the standardized Alderson head form. In particular, the back surface geometry according to the embodiment shown in FIG. 3 is configured for a wearer having a monocular pupil distance of 32 mm. The back vertex to center of rotation distance was set to 27 mm when configuring the back surface of the shield 300.

The different portions 305, 306a, 306b, 307a, 307b, 308a, 308b, 310a, 310b may be distinguished as set forth below.

There is a nose portion 305, which is located above the nose opening 312, which is formed mainly in order to comply with aesthetic and mechanical aspects. Portions 306a and 306b, corresponding to those areas a wearer is supposed to look through during every time use of the eyewear, are formed to comply with optical requirements. Therefore, the back surface geometry of these portions 306a, 306b (which include portions 307a, 307b) is configured such that for the "average wearer" non-zero minus power is established. Prism as worn of less than 0.15 prism diopter, however, is established within inner portions 307a, 307b, only. In particular, the surface shape within the portions 306a, 306b, 307a and 307b complies with the "normal" line of sight of the respective wearer's eye and takes into consideration the eye rotations of the respective eye around the center of rotation of the respective "average wearer's" eye. These portions 306a, 306b, 307a, 307b of the back surface have a freeform surface geometry. Portions 308a, 308b are transition zones to portions 310a, 310b, respectively, which according to the present embodiment shown in FIG. 3 are not optically corrected and may be frosted. These portions 310a, 310b may, however, also be formed according to the peripheral zones disclosed in U.S. Pat. No. 6,364,481 B1 which is incorporated herein by reference.

The main new feature of the invention is the fact that both portions 306a, 306b (including portions 307a, 307b) of the back surface 304 are "freeform"; they have no axis of symmetry, and the horizontal cross-section is not in the form of any standard geometric shape; such as a conicoid (ellipse, hyperbola, parabola et cetera) and yet they also have sufficient optical quality to pass ISO 12311:2013, ISO 12312-1, ANSI 280.3 and/or AS/NZS1067 standards for protective eyewear which are all incorporated herein by reference.

Figure 4:
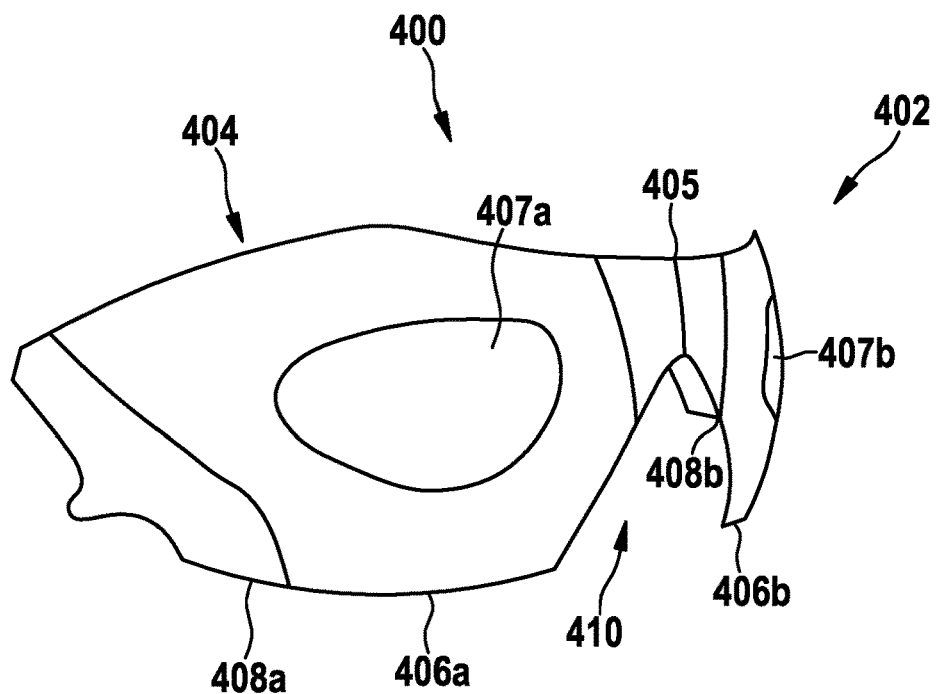
FIG. 4 is a perspective view of a second embodiment of a one-piece shield according to the invention for non-corrective unitary lens eyeglasses.

FIG. 4 shows another embodiment of a one-piece shield 400 according to the invention for mounting in a frame of non-corrective unitary lens eyeglasses. The shield 400 being molded as a single piece has a front surface 402 and a back surface 404. The front surface 402 has a predefined front surface geometry which is mainly complementary to the frame in which the shield 300 is to be mounted. In the present embodiment, the front surface has a toroidal shape.

The back surface geometry of the back surface 404 has different zones or portions 405, 406a, 406b, 407a, 407b, 408a, 408b which are distinguished by its respective local/areal geometries.

The frame with the respective temple arms is constructed to dispose the one-piece shield 400 in a predetermined local relationship with respect to a wearer's head and eyes. In the present embodiment the frame is shaped to comply to a Canadian head form. The configurations of portions 406a, 406b, 407a, 407b of the back surface geometry of the shield 400 corresponds to the explanations given with respect to the configurations of portions 306a, 306b, 307a, 307b of the one-piece shield 300 for which the Alderson head form is used. In particular, configurations of portion 406a correspond to the configurations of portion 306a, configuration of portion 406b corresponds to the configuration of portion 306b, configuration of portion 407a corresponds to the configuration of portion 306a and configuration of portion 407b corresponds to the configuration of portion 307b, respectively.

In summary, there is a nose portion 405, which is located above the nose opening 410 which is formed in order to comply with aesthetic and mechanical aspects, mainly. Portions 406a and 406b (including portions 407a, 407b), corresponding to those areas a wearer is supposed to look through during every time use of the eyewear, are formed to comply with optical requirements. Therefore, the back surface geometry of these portions 406a, 406b (including portions 407a, 407b) is configured such that for the "average wearer" non-zero minus power and prism as worn of less than 0.15 prism diopter is established within portions 407a, 407b, while the criterion non-zero minus power is established within portions 406a, 406b but outside portions 407a, 407b, the criterion prism as worn of less than 0.15 prism diopter is not established. In particular, the surface shape within the portions 406a, 406b, 407a and 407b complies with the "normal" line of sight of the respective wearer's eye and takes into consideration the eye rotations of the respective eye around the center of rotation of the respective "average wearer's" eye. These portions 406a, 406b (including portions 407a, 407b) of the back surface 404 have a freeform surface geometry. Portions 410a, 410b are formed in order to comply with mechanical and aesthetic requirements of the eyewear.

Figure 5:
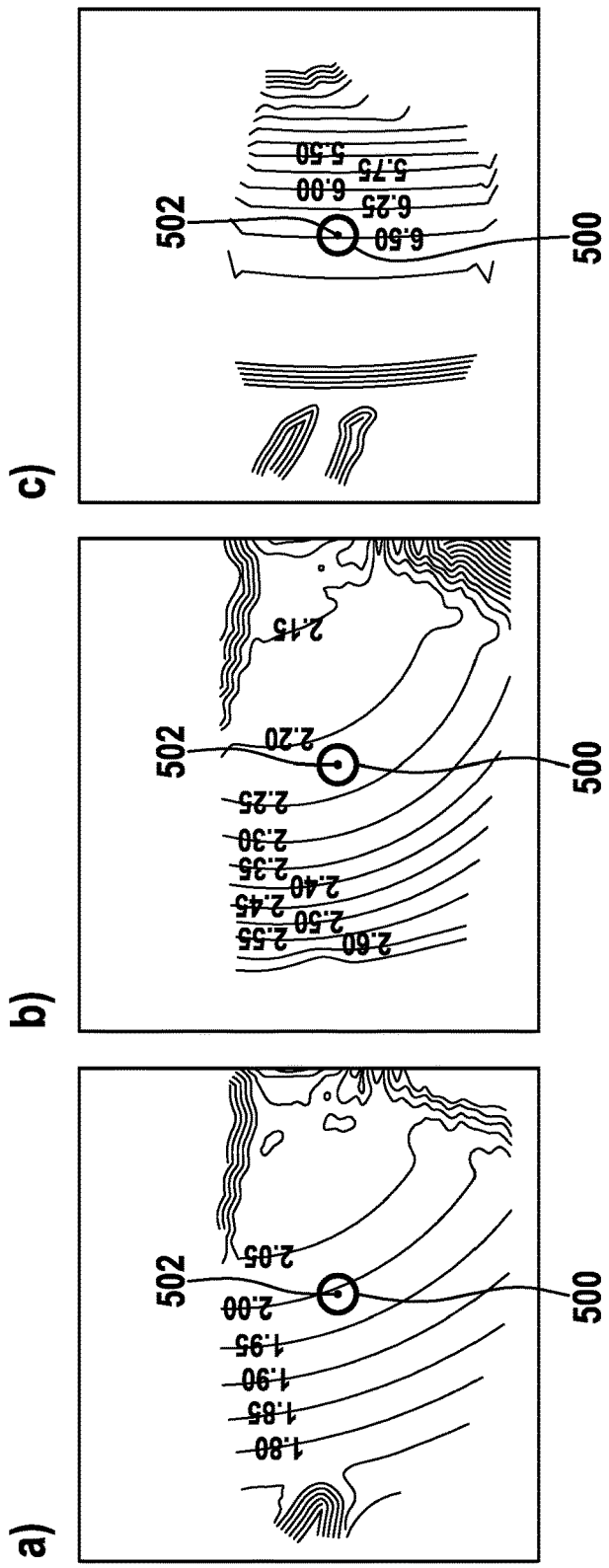
FIG. 5A is the lens thickness normal to the front of one half (nose to the right temple) of the one-piece shield shown in FIG. 3.
FIG. 5B is the lens thickness measured in local z-coordinates of the one half (nose to the right temple) shown in FIG. 5A of the one-piece shield shown in FIG. 3.
FIG. 5C is a contour plot (front surface mean power) of the one half (nose to the right temple) shown in FIGS. 5A and 5B of the one-piece shield shown in FIG. 3.

FIG. 5A shows the lens thickness (in 10 µm) normal to the front of one half (nose to the right temple) of the one-piece shield 300 shown in FIG. 3. FIG. 5B shows the lens thickness (in 10 µm) measured in local z-coordinates of the one half (nose to the right temple) shown in FIG. 5A of the one-piece shield 300 shown in FIG. 3 and FIG. 5C shows a contour plot (front surface mean power; in 0.01 D) of the one half (nose to the right temple) shown in FIGS. 5A and 5B of the one-piece shield 300 shown in FIG. 3. These plots show that the shield 300 deviates significantly from a sphere. The round circle 500 shows the position where the standard eye will be located and the center 502 thereof shows the intersection of the "normal" line of sight with the back surface 404.

It is to be mentioned that at the corresponding point of intersection of the "normal" line of sight with the front surface 402 the mean curvature of the front surface 402 is 6.5 D or greater, namely 7.5 D in the embodiment shown. Further, the thickness at that point is at least 1.95 mm measured normal to the front surface 402, namely 2.10 mm in the embodiment shown.

Figure 6:
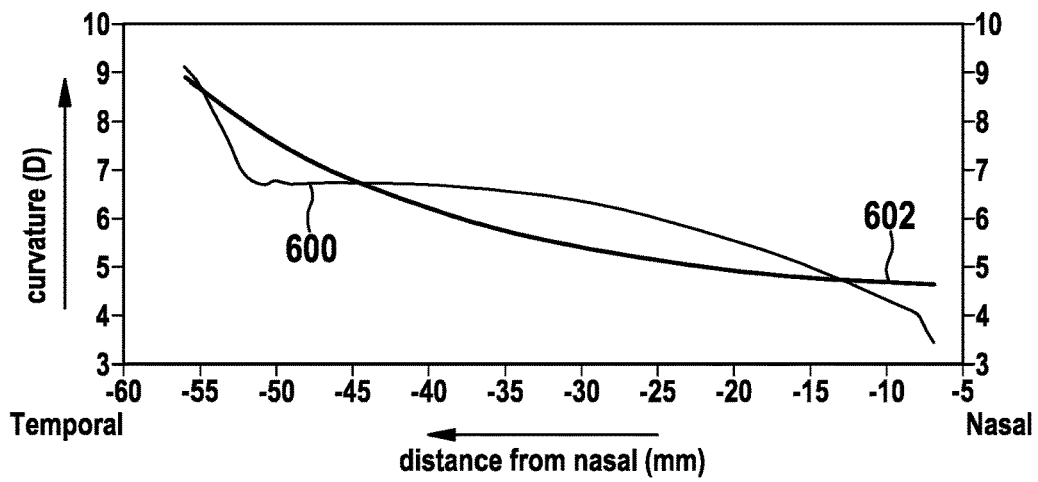
FIG. 6 is the horizontal component of the curvature taken along the horizontal meridian cross section of the optical part of one half of the one-piece shield shown in FIG. 3, along with how a "similar" elliptical lens curvature profile might look; and, FIG. 7 is a block diagram showing the main process steps of a method for configuring a one-piece shield according to the invention.

FIG. 6 shows the horizontal component of the curvature 600 (in D) taken along (distance from nasal in mm) the horizontal meridian cross section of the optical part of one half of the one-piece shield 300 shown in FIG. 3, along with how a "similar" elliptical lens curvature profile 602 might look. The unique thing which may be identified in this curvature profile 600 is the abrupt change in the gradient in the back surface geometry of the shield 300. The benefit is (arguably) a wider range of "flattish" curvature while still wrapping tightly toward the temple since both front and back surfaces are freeform.

Figure 7:
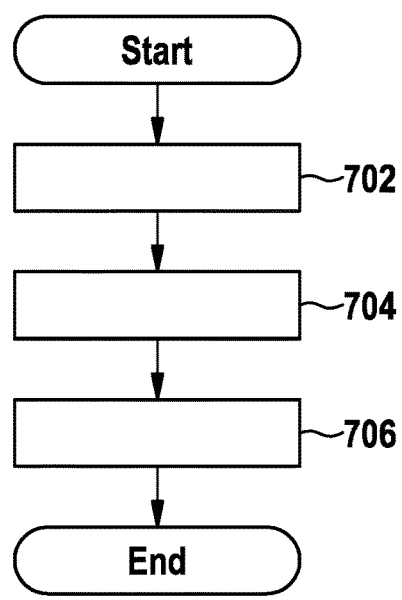

FIG. 7 shows a block diagram showing the main process steps of a method for configuring a one-piece shield according to the invention. The method comprises the steps:
  providing a front surface geometry of this shield (step 702);
  providing a predetermined local relationship of this front surface geometry with respect to a predetermined center of rotation of at least one of a wearer's eyes (step 704);
  calculating a predetermined portion of a back surface geometry of this shield attributed to the at least one of the wearer's eyes by establishing non-zero minus power and minimizing prism as worn for a plurality of wearer's lines of sight intersecting the back surface within the predetermined portion and the front surface due to eye rotations of the at least one of the wearer's eyes around the predetermined center of rotation of the at least one of the wearer's eyes, whereby the predetermined portion of the back surface geometry is a freeform surface geometry (step 706).

The step 702 may, for example, for configuring the shield 300 according to FIG. 3 comprise providing data representing the freeform shape of the front surface to a computer, which may be, for example, three dimensional lattice points. The three dimensional lattice points may be coordinates within a respective three dimensional coordinate system, such as a Cartesian coordinate system. As a further dimension the curvature at the respective three dimensional lattice point may be provided.

The step 704 may, for example, for configuring the shield 300 according to FIG. 3 comprise providing data representing the location and orientation of the free formed front surface shape and data representing the location of the predetermined center of rotation of one or both of a wearer's eyes to the computer. If the data representing the free formed front surface shape is provided in the form of three (or more) dimensional lattice points it may be sufficient to also provide the location of the predetermined center of rotation of one or both of a wearer's eyes in the form of a three dimensional lattice point.

The step 706 may, for example, comprise applying a ray-tracing method for different wearer's lines of sight and calculating the location and curvature of points for which these different wearer's lines of sight intersect the back surface within the portion(s) in order to establish the optical properties, namely non-zero minus power and minimized prism as worn. A method for conducting such a calculation is, for example, disclosed by Werner Köppen, "Konzeption and Entwicklung von Progressivgläsern", in Deutsche Optiker Zeitung DOZ 10/95, p. 42 to 46.

It is understood that the foregoing description is that of the preferred embodiments of the invention and that various changes and modifications may be made thereto without departing from the spirit and scope of the invention as defined in the appended claims.

What is claimed is:
1. A computer-implemented method for designing a one-piece shield for non-corrective unitary lens eyeglasses or safety helmets, said shield having a front surface and a back surface, the method comprising the steps of:

providing a front surface geometry of said shield;
providing a predetermined local relationship of said front surface geometry with respect to a predetermined center of rotation of at least one of a wearer's eyes; and,
calculating a predetermined portion of a back surface geometry of said shield attributed to said at least one of said wearer's eyes by establishing non-zero minus power and minimizing prism as worn for a plurality of wearer's lines of sight intersecting said back surface within said predetermined portion and said front surface due to eye rotations of said at least one of said wearer's eyes around said predetermined center of rotation of said at least one of said wearer's eyes wherein said non-zero minus power within said portion is less than 0.12 D and said predetermined portion of said back surface geometry defines a freeform surface geometry having no axis of symmetry.

2. The method of claim 1, wherein said non-zero minus power within said portion is less than at least one of the following: 0.09 D; and, 0.05 D.

3. The method of claim 1, wherein said non-zero minus power within said portion exceeds at least one of the following: 0.01 D; 0.02 D; 0.03 D; and, 0.04 D.

4. The method of claim 1, wherein said minimizing prism comprises minimizing vertical prism as worn and/or minimizing horizontal prism as worn.

5. The method of claim 1, wherein said plurality of wearer's lines of sight intersecting said back surface within said predetermined portion and said front surface due to eye rotations of said at least one of said wearer's eyes around said predetermined center of rotation of said at least one of said wearer's eyes for which non-zero minus power is established and prism is minimized comprise more than at least one of the following: 10 different wearer's lines of sight; 20 different wearer's lines of sight; and, 30 different wearer's lines of sight.

6. A computer-implemented method for designing a one-piece shield for non-corrective unitary lens eyeglasses or safety helmets, said shield having a front surface and a back surface, the method comprising the steps of:
providing a front surface geometry of said shield;
providing a predetermined local relationship of said front surface geometry with respect to a predetermined center of rotation of at least one of a wearer's eyes; and,
calculating a predetermined portion of a back surface geometry of said shield attributed to said at least one of said wearer's eyes by establishing non-zero minus power and minimizing prism as worn for a plurality of wearer's lines of sight intersecting said back surface within said predetermined portion and said front surface due to eye rotations of said at least one of said wearer's eyes around said predetermined center of rotation of said at least one of said wearer's eyes, wherein said non-zero minus power within said portion is less than 0.12 D, whereby said predetermined portion of said back surface geometry is a freeform surface geometry;
wherein said predetermined portion is more than at least one of the following: 0.1 cm$^2$ in size; 0.25 cm$^2$ in size; 0.5 cm$^2$ in size; and, 0.75 cm$^2$ in size.

7. A computer-implemented method for designing a one-piece shield for non-corrective unitary lens eyeglasses or safety helmets, said shield having a front surface and a back surface, the method comprising the steps of:
providing a front surface geometry of said shield;
providing a predetermined local relationship of said front surface geometry with respect to a predetermined center of rotation of at least one of a wearer's eyes; and,
calculating a predetermined portion of a back surface geometry of said shield attributed to said at least one of said wearer's eyes by establishing non-zero minus power and minimizing prism as worn for a plurality of wearer's lines of sight intersecting said back surface within said predetermined portion and said front surface due to eye rotations of said at least one of said wearer's eyes around said predetermined center of rotation of said at least one of said wearer's eyes, wherein said non-zero minus power within said portion is less than 0.12 D, whereby said predetermined portion of said back surface geometry is a freeform surface geometry;
wherein said predetermined portion is less than at least one of the following: 2.5 cm$^2$ in size; 2.0 cm$^2$ in size; 1.5 cm$^2$ in size; and, 1.0 cm$^2$ in size.

8. A computer-implemented method for designing a one-piece shield for non-corrective unitary lens eyeglasses or safety helmets, said shield having a front surface and a back surface, the method comprising the steps of:
providing a front surface geometry of said shield;
providing a predetermined local relationship of said front surface geometry with respect to a predetermined center of rotation of at least one of a wearer's eyes; and,
calculating a predetermined portion of a back surface geometry of said shield attributed to said at least one of said wearer's eyes by establishing non-zero minus power and minimizing prism as worn for a plurality of wearer's lines of sight intersecting said back surface within said predetermined portion and said front surface due to eye rotations of said at least one of said wearer's eyes around said predetermined center of rotation of said at least one of said wearer's eyes, wherein said non-zero minus power within said portion is less than 0.12 D, whereby said predetermined portion of said back surface geometry is a freeform surface geometry;
wherein said predetermined portion attributed to said at least one of said wearer's eyes and said predetermined portion attributed to the other of said wearer's eyes do not intersect each other.

9. A computer-implemented method for designing a one-piece shield for non-corrective unitary lens eyeglasses or safety helmets, said shield having a front surface and a back surface, the method comprising the steps of:
providing a front surface geometry of said shield;
providing a predetermined local relationship of said front surface geometry with respect to a predetermined center of rotation of at least one of a wearer's eyes; and,
calculating a predetermined portion of a back surface geometry of said shield attributed to said at least one of said wearer's eyes by establishing non-zero minus power and minimizing prism as worn for a plurality of wearer's lines of sight intersecting said back surface within said predetermined portion and said front surface due to eye rotations of said at least one of said wearer's eyes around said predetermined center of rotation of said at least one of said wearer's eyes, wherein said non-zero minus power within said portion is less than 0.12 D, whereby said predetermined portion of said back surface geometry is a freeform surface geometry;
wherein said calculating step comprises establishing zero vertical prism as worn and zero horizontal prism as worn for at least one predetermined wearer's line of sight, whereby said at least one predetermined line of sight is at least one of the theoretical straight ahead line of sight, a measured straight ahead line of sight of an individual, a theoretical functional line of sight or a measured functional line of sight of an individual.

10. A method for making a one-piece shield for non-corrective unitary lens eyeglasses or safety helmets, said shield having a front surface and a back surface, the method comprising the steps of:

provide a front surface geometry of said shield;

providing a predetermined local relationship of said front surface geometry with respect to a predetermined center of rotation of at least one of a wearer's eyes;

calculating a predetermined portion of a back surface geometry of said shield attributed to said at least one of said wearer's eyes by establishing non-zero minus power and minimizing prism as worn for a plurality of wearer's lines of sight intersecting said back surface within said predetermined portion and said front surface due to eye rotations of said at least one of said wearer's eyes around said predetermined center of rotation of said at least one of said wearer's eyes wherein said non-zero minus power within said portion is less than 0.12 D and said predetermined portion of said back surface geometry defines a freeform surface geometry having no axis of symmetry; and, molding said shield with or without a frame as a single molded piece.

11. A computer program comprising a program code stored on a non-transitory computer readable medium, the program code being for designing a one-piece shield for non-corrective unitary lens eyeglasses or safety helmets, the shield having a front surface and a back surface, wherein said program code is configured, when executed by a processor, to:

provide a front surface geometry of said shield;

provide a predetermined local relationship of said front surface geometry with respect to a predetermined center of rotation of at least one of a wearer's eyes; and, calculate a predetermined portion of a back surface geometry of said one-piece shield attributed to said at least one of said wearer's eyes by establishing non-zero minus power and minimizing prism as worn for a plurality of wearer's lines of sight intersecting said back surface within said predetermined portion and said front surface due to eye rotations of said at least one of said wearer's eyes around said predetermined center of rotation of said at least one of said wearer's eyes wherein said non-zero minus power within said portion is less than 0.12 D and said predetermined portion of said back surface geometry defines a freeform surface geometry having no axis of symmetry.

12. A non-transitory computer readable storage medium having a computer program stored thereon for designing a one-piece shield for non-corrective unitary lens eyeglasses or safety helmets, the shield having a front surface and a back surface, wherein said computer program comprises a program code configured, when executed by a processor, to:

provide a front surface geometry of said shield;

provide a predetermined local relationship of said front surface geometry with respect to a predetermined center of rotation of at least one of a wearer's eyes; and, calculate a predetermined portion of a back surface geometry of said one-piece shield attributed to said at least one of said wearer's eyes by establishing non-zero minus power and minimizing prism as worn for a plurality of wearer's lines of sight intersecting said back surface within said predetermined portion and said front surface due to eye rotations of said at least one of said wearer's eyes around said predetermined center of rotation of said at least one of said wearer's eyes wherein said non-zero minus power within said portion is less than 0.12 D and said predetermined portion of said back surface geometry defines a freeform surface geometry having no axis of symmetry.

* * * * *